United States Patent [19]

Hui et al.

[11] Patent Number: 4,942,252

[45] Date of Patent: Jul. 17, 1990

[54] SYNTHESIS OF PHOSPHORUS AND ARSENIC, HALIDES AND HYDRIDES

[75] Inventors: Benjamin C. Hui, Peabody, Mass.; Jörg Lorberth, Weimar-Niederweimar, Fed. Rep. of Germany

[73] Assignee: CVD Incorporated, Woburn, Mass.

[21] Appl. No.: 232,729

[22] Filed: Aug. 16, 1988

[51] Int. Cl.$^5$ .............................. C07F 9/72; C07F 9/50
[52] U.S. Cl. .......................................... 556/70; 568/16
[58] Field of Search ............................ 556/70; 568/16

[56] References Cited

U.S. PATENT DOCUMENTS

| | | | |
|---|---|---|---|
| 3,366,655 | 1/1968 | Weingarten et al. | 556/70 |
| 3,432,534 | 3/1969 | Remes et al. | 556/70 |
| 4,734,514 | 3/1988 | Melas et al. | 556/70 |

FOREIGN PATENT DOCUMENTS

| | | | |
|---|---|---|---|
| 0181706 | 5/1988 | European Pat. Off. | 556/70 |
| 173796 | 1/1922 | United Kingdom | 556/70 |

OTHER PUBLICATIONS

Maier et al., *JACS* 79, 5884 (1957).
Evans et al., *Trans. Faraday Soc.*, 44, 189 (1948).
Valeur et al., *Bull. Soc. Chim. Fr.*, 41, 1318 (1927).
Marquardt *Berichte* 20, 1516 (1887).
Burton, *J. Chem. Soc.* 450 (1926).
Cullen, W. R. et al., *Can. J. Chem., 47, 2137 (1969)*.
Doak & Freedman, *Organometallic Compounds of Arsenic, Antimony, and Bismuth*, John Wiley & Sons, Inc., (1970), pp. 85–86, 437–438.
Evans, A. G. et al., Trans Faraday Soc., 44, 189 (1948).
Fitzpatrick, H. D. N. et al., *J. Chem. Soc.*, 3542 (1950).
Gibson et al., *J. Chem. Soc.* 2518 (1931).
Kharasch et al., *J. Org. Chem.*, 14, 429 (1949).
Maier, L., *Inorganic Synthesis* 7:82 (1963).
Parkes, G. D. et al., *J. Chem. Soc.*, 429 (1947).
Wiberg, E. et al., Z. Naturforsch, B, 11, 751 (1956).
Wiberg, E. et al., Z. Naturforsch, B, 12, 127 (1957).

*Primary Examiner*—Paul F. Shaver
*Attorney, Agent, or Firm*—Gerald K. White

[57] ABSTRACT

Method for synthesizing alkyl halides of phosphorus, arsenic, or antimony from the corresponding phosphorus, arsenic, or antimony alkyl and phosphorus, arsenic, or antimony halide. An improved synthesis of alkyl phosphorus or arsenic hydrides from the corresponding alkyl phosphorus, arsenic, or antimony halides is also disclosed.

19 Claims, No Drawings

SYNTHESIS OF PHOSPHORUS AND ARSENIC, HALIDES AND HYDRIDES

BACKGROUND

The present invention relates to the synthesis of compounds having the formula:

$$R_yMX_{(3-y)} \qquad (1)$$

wherein R is lower alkyl, M is arsenic or phosphorus, X is a halogen, and y is 1 or 2. (R, M, and X retain these definitions throughout this specification, unless the context indicates otherwise.) The invention also relates to methods for preparing compounds of the formula:

$$R_yMH_{(3-y)} \qquad (2)$$

wherein H is hydride and the other substituents are like those of formula (1), from compounds of formula (1).

Compounds of formula (2), have recently found favor as reactants for metal organic chemical vapor deposition of III/V compound semiconductor films for electronic, optical, and other technologies. The utility of such arsenic and phosphorus compounds for metal organic chemical vapor deposition is disclosed in U.S. Pat. No. 4,734,514, issued to Melas et al. on Mar. 29, 1988. That patent is hereby incorporated by reference herein in its entirety.

While the alkyl hydrides of formula (2) are very useful compounds, their synthesis has been long and complicated, with a low yield. In Example 1 of the Melas patent previously incorporated by reference, the synthesis of diethylarsine using arsenic trichloride as a starting material requires a sequence of four reactions. The first three reactions are required to form diethylchloroarsine — a compound according to formula (1). Thus, one problem facing the art has been how to form the compounds of formula (1) more directly and with higher yields.

The arsenic or phosphorus compounds of formula (1) have been reported to be synthesized by directly reacting the corresponding alkyl halide with arsenic or phosphorus at 70° C. in the presence of copper as a catalyst, according to the equation;

$$3\ RX + 2\ M \xrightarrow{Cu} R_2MX + RMX_2 \qquad (3)$$

(L. Maier, *Inorganic Synthesis* 7:82 (1963).) (The antimony synthesis hasn't been reported.) Unfortunately, the yield of the halide has been reported to be quite low, particularly when is arsenic and the R group is ethyl.

Another reaction scheme which provides formula (1) halides is found in Kharasch, et al., *J. Org. Chem.* 14, 429 (1949):

$$R_4Pb + 2\ AsCl_3 \rightarrow R_2PbCl_2 + 2\ RAsCl_2 \qquad (4)$$

$$R_2PbCl_2 + AsCl_3 \rightarrow RAsCl_2 + PbCl_2 + RCl \qquad (5)$$

This can be a one-step synthesis. The analogous synthesis for phosphorus is:

$$Et_4Pb + 3\ PCl_3 \rightarrow 3\ EtPCl_2 + PbCl_2 + EtCl \qquad (6)$$

However tetraalkyl lead compounds are toxic, and lead as an impurity might damage III/V films formed from the resulting product.

Another multistep synthesis of formula (1) halides is found in Burton, *J. Chem. Soc.* 450 (1926) and Gibson, et al., *J. Chem. Soc.* 2518 (1931), as follows:

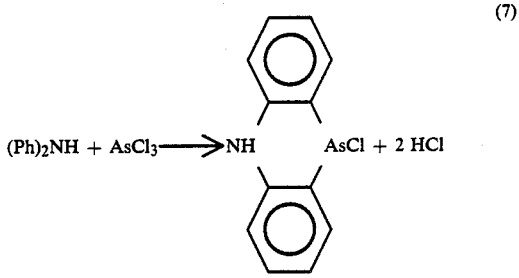

(7)

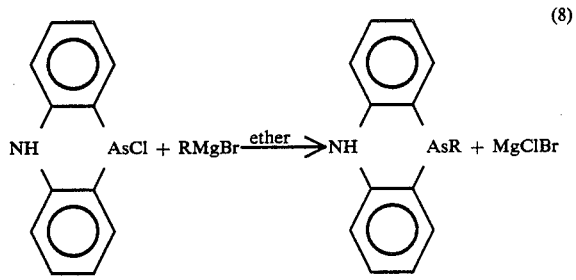

(8)

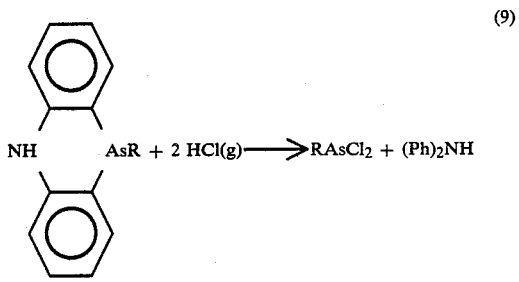

(9)

(In the formulas herein, "Ph" is phenyl).

The yield of this reaction sequence is low.

Other, less pertinent syntheses of the formula (1) halides are also known. (See Doak & Freeman, *Oranometallic Compounds of Arsenic, Antimony, and Bismuth*, John Wiley & Sons, Inc., 1970).

The following two reactions are known for triphenylarsine (G. D. Parkes, R. J. Clarke and B. H. Thewlis. *J. Chem. Soc.* 429 (1947); A. G. Evans and E. Warhurst, *Trans Faraday Soc.*, 44. 189 (198); H. D. N. Fitzpatrick, S. R. C. Hughes, and E. A. Moelwyn-Hughes, *J. Chem. Soc.* 3542 (1950)), and both monochloro and dichloroarsine derivatives can be made this way:

$$2\ (Ph)_3As + AsCl_3 \rightarrow 3\ (Ph)_2AsCl \qquad (9)$$

$$(Ph)_3As + 2\ AsCl_3 \rightarrow 3\ (Ph)AsCl_2 \qquad (10)$$

However, these reactions are unknown for alkyl arsines, and chloroalkylarsines cannot be made in this manner. For example, the reaction of trimethylarsine with arsenic trichloride has been reported to form only the stable addition compound:

$$(CH_3)_3As \cdot AsCl_3 \qquad (11)$$

(A. Valeur and P. Gaillot. *Bull. Soc. Chim. Fr.*, 41. 1318 (1927).

While not intending to be bound by this theory, the inventors believe that trialkylarsines have not previously been recognized as being reactive in the present context because triphenylarsine is far less basic than trialkylarsines. As a result, triphenylarsine does not form a stable adduct with arsenic trichloride and is readily reactive with additional arsenic trichloride or triphenylarsine to form products according to formula (1) above. On the other hand, attempts to form the products of formula (1) directly from the corresponding alkylarsine and trihaloarsine have failed because a stable adduct of these reactants forms and does not easily react to form the desired products.

Redistribution reactions take place readily for both alkyl and aryl derivatives of bismuth. This perhaps may be attributed to the weak bismuth to carbon bonds in these compounds facilitating the exchange of R and X (halogen) groups. (A. Marguardte, *Berichte* 20 1516 (1887)).

$$Me_3Bi + 2\ BiBr_3 \rightarrow 3\ MeBiBr_2 \tag{12}$$

$$Et_3Bi + 2\ BiBr_3 \rightarrow 3\ EtBiBr_2 \tag{13}$$

$$2\ Ph_3Bi + BiCl_3 \rightarrow 3\ Ph_2BiCl \tag{14}$$

Both primary and secondary arsines of formula (2) are generally prepared by reducing a different arsenic compound with a reducing agent. Thus, alkylarsonic (or alkylarsinic) acids and alkylchloroarsines are common arsenic starting sources which can be reduced with zinc dust, zinc amalgam or zinc-copper couple in aqueous hydrochloric acid. For example;

$$Me_2AsO(OH) + 4H \xrightarrow{Zn/Hg}{HCl} Me_2AsH + 2\ H_2O \tag{15}$$

See W. R. Cullen and W. R. Leeder, *Can. J. Chem.*, 47 2137 (1969))

Lithium aluminum hydride has also been used, but the results are generally less satisfactory with poorer yields:

$$PhAsCl_2 + LiAlH_4 \xrightarrow{ether}{H_2O} PhAsH_2 \tag{16}$$

(See E. Wiberg and K. Modritzer, *Z. Naturforsch, B*, 11. 751 (1956) and B, 12, 127 (1957))

Arsines made by the routes of equations (15) and (16) might be contaminated with zinc, mercury or copper and subsequently might damage the III-V films formed from these products. The water used in reaction (16) can produce oxygen-containing impurities in the films.

SUMMARY OF THE INVENTION

A first aspect of the invention is a method of synthesizing a compound having formula (1) above from the following starting materials:

$$R_3M \text{ and} \tag{17}$$

$$X_3M \tag{18}$$

wherein M, R and X are defined as before. The starting materials are reacted according to the following equation:

$$y\ R_3M\ (3-y)\ X_3M \rightarrow 3\ R_yMX_{(3-y)} \tag{19}$$

A second aspect of the invention is a method for forming alkyl arsenic hydride (also called an alkylarsine) or dialkylarsine) which is essentially free of water or harmful metallic impurities. In the present method, instead of adding water to the reaction mixture (which is described in Example 1 of the previously incorporated U.S. patent at column 15, line 62 to column 16, line 10), the precursor of formula:

$$R_yMH_{(3-y)}AlH_3 \tag{20}$$

is distilled under anhydrous conditions to directly isolate the corresponding dialkyl arsine. By using this procedure, which is contrary to the accepted practice, a product which is inherently free of water is produced.

DETAILED DESCRIPTION OF THE INVENTION

For the first synthesis summarized above, one of the reactants is a Group V alkyl of formula (17) above. R is lower alkyl, which is defined herein as methyl, ethyl, propyl, or butyl, including all the isomers of propyl and butyl. M is selected from the group consisting of arsenic or phosphorus. Arsenic is specifically contemplated due to its proven value for chemical vapor deposition processes. The R moieties of this material are selected according to the final compound desired. One particular reactant contemplated herein is triethyl arsine. Many trialkyl arsines are known.

The other reactant used in the present process is a halide of formula (18) above. Assuming a single compound is to be synthesized, M is the same in formulas (17) and (18). The respective M moieties can be different, however, if a mixture of compounds is contemplated as the end product. In formula (18). X is a halide, preferably chloride, bromide, or iodide. Chloride is specifically contemplated for use herein. The reactants of formulas (17) and (18) undergo a redistribution reaction to form products according to formula (1).

The following is an illustration of the present synthesis using triethylarsine and arsenic trichloride. As the first step of the synthesis, triethylarsine is added to arsenic trichloride (both are liquids at room temperature). A white, crystalline, solid, 1:1 adduct is formed immediately, regardless of the ratio of the reactants used (i.e., 2:1, 1:2, or 1:1):

$$2\ Et_3As + 2\ AsCl_3 \rightarrow (Et_3As.AsCl_3)_2 \tag{21}$$

The adduct can be is isolated and the x-ray crystal structure has been determined.

Once this adduct is formed, it will react further with more triethylarsine or arsenic trichloride in a second step according to one of the following equations:

$$(Et_3As.AsCl_3)_2 + 2\ Et_3As \rightarrow 6\ Et_2AsCl \tag{22}$$

$$(Et_3As.AsCl_3)_2 + 2\ AsCl_3 \rightarrow 6\ EtAsCl_2 \tag{23}$$

The reactions of the adduct with either triethylarsine or arsenic trichloride require long reaction times (about 30 hours) and vigorous heating. It is very likely that previous investigators failed to identify the proper experimental conditions for the present reaction in the past and only reported the formation of the adduct.

The initial reaction is carried out in a solvent, e.g. hexane or petroleum ether. After the formation of the adduct the solvent must be removed because heating at a much higher temperature is required in the next step. Extreme care must be taken during solvent removal so the second reactant in equation (22) or (23) (depending on the desired end product) is conserved. Failing to do this will change the stoichiometry and thus drastically reduce the yield. As a precaution, the adduct cam be generated first by reacting triethylarsine and arsenic trichloride in a 1:1 ratio, and, after removal of solvent, an additional mole of triethylarsine (or arsenic trichloride) can be added (see Example 3).

The alkyl halides made according to the present invention can be used as precursors to the corresponding alkyl hydrides. The latter compounds are directly useful for metal organic chemical vapor deposition. Several reactions may be used to exchange hydride groups for halide groups, one of which is described in the final part of Example 1 of the U.S. patent previously incorporated by reference.

Another way to proceed from the halide to the corresponding hydride is as follows. Once the alkyl phosphorus, arsenic, or antimony halide is complexed with lithium aluminum hydride as described in Example 1 of U.S. Pat. No. 4,734,514, the mixture is distilled under anhydrous conditions, instead of adding water as has previously been done. The reaction thus proceeds as follows, starting from the addition of lithium aluminum hydride:

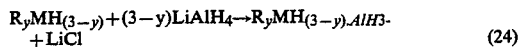

$$R_yMH_{(3-y)} + (3-y)LiAlH_4 \rightarrow R_yMH_{(3-y)}.AlH_3 + LiCl \quad (24)$$

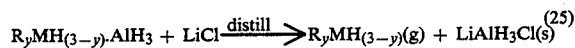

$$R_yMH_{(3-y)}.AlH_3 + LiCl \xrightarrow{distill} R_yMH_{(3-y)}(g) + LiAlH_3Cl(s) \quad (25)$$

The resulting product is very free of water and other contaminants, down to a 1 or 2 parts per million level.

EXAMPLE 1: SYNTHESIS OF DIETHYLARSENIC CHLORIDE 196 grams (1.204 mol of triethylarsine diluted with 500 ml of petroleum ether at 40°–60° C. in a 1 liter flask, were reacted with 109 grams (0.602 mol) of arsenic trichloride, diluted with 50–100 ml petroleum ether, by adding the arsenic trichloride solution dropwise at room temperature. There was almost no reaction heat.

After the addition was complete (in about 30 minutes), the mixture was refluxed with a hot water bath (no heating mantle) for 2–3 hours. The suspension or solution was transferred in two or three portions to a 500 ml flask (to reduce volume and from that flask petroleum ether was slowly distilled at ambient pressure. The oil bath temperature never exceeded 80° C.

After distillation of the petroleum ether, the temperature was slowly increase to a maximum of 140° C. A white to faintly brownish (sometimes also faintly pink) colored precipitate formed. The precipitate melted sharply at 120° C. and the liquid deposited black arsenic during the melting process.

At this temperature a bubbler was placed on top of the flask and the mixture was heated with stirring for 20 hours. The result after that procedure was a black viscous liquid. The product was evaporated and condensed in vacuo at about 0.1 mm pressure from flask to flask via U-glass tubing using a heating mantle set to stage I, full power for about 5 hours. A colorless liquid (sometimes contaminated with black arsenic due to splashing) having a boiling point of 151°–152° C. at 740 mm pressure resulted. This product was recondensed for purity in the same manner (flask to flask).

The diethylarsenic chloride obtained by this procedure was rather pure and did not colorize during reduction with LiAlH$_4$. The combined yield of three of these runs was 620 g. of diethylarsenic chloride, corresponding to about 68% of theory.

EXAMPLE 2: SYNTHESIS OF DIETHYLARSINE

Lithium aluminum hydride 7.21 g = 0.190 mol) was suspended in diethyl ether ad diethylarsenic chloride made according to Example 1 (42.62 g = 0.253 mol), diluted with diethyl ether, was added dropwise under an argon atmosphere. A vigorous exothermic reaction took place; the flask was cooled with ice water. The dropping rate was adjusted to allow gentle reflux of the ether solvent. The resulting diethylarsine was very volatile and extremely sensitive to oxygen, as indicated by immediate formation of white fumes.

After adding the diethylarsenic chloride, the cooling bath was removed and reflux continued for 1 hour.

All volatiles were then immediately condensed in vacuo. The reaction flask was heated with boiling water. After two hours, only traces of Product were still condensing into the collecting flask.

The diethyl ether was removed at ambient pressure at an oil bath temperature of about 80° C. The remaining liquid consisted of pure diethylarsine, a colorless liquid having a boiling point of 98 to 100° C. at 760 mm. pressure. The yield was 5.50 g., 75.2% of theory.

By using twice as many mols of diethylarsenic chloride as of lithium aluminum hydride in a subsequent run, the yield was increased to 79% of theory. Thus, this ratio of ingredients is preferred.

EXAMPLE 3 — SYNTHESIS OF DIETHYLARSENIC CHLORIDE 319 grams (1.97 mol) of triethylarsine diluted with 1.2 liters of hexane were reacted with 356 grams (1.96 mole) of arsenic trichloride as described in Example 1. The hexane was removed to leave behind the 1:1 adduct shown in formula (21) above.

Another 319 grams of triethylarsine were added to the adduct in the flask and the mixture was heated to a maximum of 140° C. as in Example 1 for about 30 hours. The product, diethylarsenic chloride, was isolated similarly by distillation.

EXAMPLE 4 — SYNTHESIS OF ETHYLARSENIC DICHLORIDE 100 grams (0.61 mol) of triethylarsine and 225 grams (1.24 mol) of arsenic trichloride are reacted in 500 ml of hexane in a 1 liter flask. As in Example 1, the mixture is refluxed for 2–3 hours. The solvent is carefully removed and the temperature slowly raised to a maximum of 140° C. After heating the reactants for about 30 hours the product, ethylarsenic dichloride, is isolated by distillation (boiling point 155° C.).

EXAMPLE 5 — SYNTHESIS OF DI-BUTYLPHOSPHORUS CHLORIDE

As in Example 1, tributylphosphine (1.0 mole) is reacted with phosphorus trichloride (0.5 mole) in petroleum ether, and di-butyl phosphorus chloride can be isolated by vacuum distillation.

We claim:

1. A method of synthesizing a compound having the formula:

$$R_yMX_{(3-y)}$$

wherein M is selected from the group consisting of phosphorus and arsenic, R is lower alkyl, X is halogen, and y is 1 or 2, comprising the steps of:
- A. providing as starting materials compounds having the formulas, $R_3M$ and $X_3M$ wherein each M is the same element and M, X, and R are defined as before;
- B. reacting said starting materials to form an intermediate complex according to the following reaction:

$$2\ R_3M + 2MX_3 \rightarrow (R_3M.MX_3)_2;\ \text{and}$$

- C. reacting said intermediate complex with two additional equivalents of one of said starting materials according to a selected one of the following equations:

$$2\ R_3M + (R_3M.MX_3)_2 \rightarrow 6\ R_2MX$$

$$2\ MX_3 + (R_3M.MX_3)_2 \rightarrow 6\ RMX_2$$

thereby providing the product:

$$R_yMX_{(3-y)}$$

2. The method of claim 1, wherein R is ethyl.
3. The method of claim 1, wherein X is chloride.
4. The method of claim 1, wherein M is arsenic.
5. The method of claim 1, wherein y is 1.
6. The method of claim 1, wherein y is 2.
7. The method of claim 1, wherein R is ethyl, y is 1, M is arsenic, and X is chloride.
8. The method of claim 1, wherein R is ethyl, y is 2, M is arsenic, and X is chloride.
9. The method of claim 1, wherein y is 1 and the second equation of said step C is followed.
10. The method of claim 1, wherein y is 2 and the first equation of said step C is followed.
11. The method of claim 1, wherein said step B is carried out in the presence of a solvent.
12. The method of claim 11, wherein said solvent is substantially removed prior to commencing said step C.
13. The method of claim 1, wherein said step B is carried out in the presence of at least two additional equivalents in excess of the stoichiometric amount of one of said starting materials and step C is carried out by reacting the product of said step B with said at least two additional equivalents of one of said starting materials.

14. A method of synthesizing a compound having the formula:

$$R_yMX_{(3-y)}$$

wherein M is selected from the group consisting of phosphorus and arsenic, R is lower alkyl, X is halogen, and y is 1 or 2, comprising the steps of:
- A. providing, as starting materials, compounds having the formulas $R_3M$ and $X_3M$ in which each M is the same element and M, R, and X are defined as above;
- B. dissolving said R, M in a solvent, thereby forming a solution of $R_3M$;
- C. dissolving said $X_3M$ in a solvent, thereby forming a solution of $X_3M$;
- D. mixing said solution of $X_3M$ with said solution of $R_3M$ for a sufficient time at a sufficient temperature to produce an adduct having the formula:

$$(R_3M.MX_3)_2;$$

- E. removing said solvents from said adduct; and
- F. heating said adduct with an excess of one of said $R_3M$ and said $X_3M$, in the absence of solvents, for a sufficient time at a sufficient temperature to produce a product consisting essentially of at least one compound of formula:
$R_yMX_{(3-y)}$ 15. The method of claim 14, wherein the temperature of said step F is between the melting and boiling temperatures of said adduct and the time of said step F is at least about 20 hours.
16. The method of claim 15, wherein the temperature of said step F is about 140° C.
17. The method of claim 16, wherein the time of said step F is about 30 hours.
18. The method of claim 14, wherein the temperature of said step D is from about 40° C. to about 60° C. and the time of said step D is from about 2 to 3 hours.
19. The method of claim 14, wherein each said solvent is selected from the group consisting of hexane, petroleum ether, or a mixture thereof.

* * * * *

UNITED STATES PATENT AND TRADEMARK OFFICE
CERTIFICATE OF CORRECTION

PATENT NO. : 4,942,252

DATED : July 17, 1990

INVENTOR(S) : Hui et al.

It is certified that error appears in the above-identified patent and that said Letters Patent is hereby corrected as shown below:

Abstract should read:

> Method for synthesizing alkyl halides of phosphorus or arsenic from the corresponding phosphorus or arsenic alkyl and phosphorus or arsenic halide. An improved synthesis of alkyl phosphorus or arsenic hydrides from the corresponding alkyl phosphorus or arsenic halides is also disclosed.

At column 1, line 53, "when is" should be -- when M is --.

At column 2, line 52, "(198)" should be -- (1948) --.

At column 3, line 20, "Marguardte," should be -- Marquardt, --.

UNITED STATES PATENT AND TRADEMARK OFFICE
CERTIFICATE OF CORRECTION

PATENT NO. : 4,942,252

DATED : July 17, 1990

INVENTOR(S) : Hui et al.

It is certified that error appears in the above-identified patent and that said Letters Patent is hereby corrected as shown below:

At column 4, line 16, "corresponding dialkyl" should be -- corresponding alkylarsine or dialkyl --.

At column 4, line 38, "(18)." should be -- (18), --.

At column 5, line 9, "cam" should be -- can --.

At column 5, line 32, the formula should be corrected to read:

"(24) $R_y MX_{(3-y)} + (3-y)LiAlH_4 \longrightarrow R_y MH_{(3-y)} \cdot AlH_3$"

At column 5, line 43, "(1.204 mol" should be -- (1.204 mol) --.

At column 5, line 53, "volume" should be -- volume) --.

At column 5, line 57, "increase" should be -- increased --.

UNITED STATES PATENT AND TRADEMARK OFFICE
CERTIFICATE OF CORRECTION

PATENT NO. : 4,942,252
DATED : July 17, 1990
INVENTOR(S) : Hui et al.

It is certified that error appears in the above-identified patent and that said Letters Patent is hereby corrected as shown below:

At column 6, line 13, "ad" should be -- and --.

At column 6, line 27, "Product" should be -- product --.

At column 6, line 33, "5.50 g." should be -- 25.50 g. --.

At column 8, line 19, "$X_3$in" should be -- $X_3M$ in --.

Signed and Sealed this

Twenty-sixth Day of October, 1993

Attest:

BRUCE LEHMAN

*Attesting Officer*    *Commissioner of Patents and Trademarks*